United States Patent
Bang et al.

(10) Patent No.: US 11,857,652 B2
(45) Date of Patent: Jan. 2, 2024

(54) DENTAL WRAP, DENTAL KIT COMPRISING THE SAME, METHOD OF USING THE SAME, AND METHOD FOR WHITENING TEETH USING THE SAME

(71) Applicant: LG Household & Health Care Ltd., Seoul (KR)

(72) Inventors: Seong-Eun Bang, Seoul (KR); Yong-Beom Jeong, Seoul (KR); Jae-Hyun Ahn, Seoul (KR)

(73) Assignee: LG Household & Health Care Ltd.

( * ) Notice: Subject to any disclaimer, the term of this patent is extended or adjusted under 35 U.S.C. 154(b) by 326 days.

(21) Appl. No.: 17/147,059

(22) Filed: Jan. 12, 2021

(65) Prior Publication Data

US 2021/0212907 A1    Jul. 15, 2021

(30) Foreign Application Priority Data

Jan. 13, 2020   (KR) .................. 10-2020-0004331
Jan. 5, 2021    (KR) .................. 10-2021-0000923

(51) Int. Cl.
```
A61K 8/02      (2006.01)
A61K 8/81      (2006.01)
A61K 8/73      (2006.01)
A61K 8/34      (2006.01)
A61K 8/98      (2006.01)
A61K 8/04      (2006.01)
A61K 8/22      (2006.01)
A61K 8/19      (2006.01)
A61K 8/49      (2006.01)
A61K 8/92      (2006.01)
A61K 8/24      (2006.01)
A61Q 11/00     (2006.01)
```

(52) U.S. Cl.
CPC ............ *A61K 8/0208* (2013.01); *A61K 8/042* (2013.01); *A61K 8/19* (2013.01); *A61K 8/22* (2013.01); *A61K 8/24* (2013.01); *A61K 8/34* (2013.01); *A61K 8/345* (2013.01); *A61K 8/49* (2013.01); *A61K 8/4973* (2013.01); *A61K 8/731* (2013.01); *A61K 8/732* (2013.01); *A61K 8/8147* (2013.01); *A61K 8/8176* (2013.01); *A61K 8/922* (2013.01); *A61K 8/987* (2013.01); *A61Q 11/00* (2013.01); *A61K 2800/30* (2013.01); *A61K 2800/56* (2013.01); *A61K 2800/87* (2013.01); *A61K 2800/882* (2013.01); *A61K 2800/92* (2013.01)

(58) Field of Classification Search
CPC . A61K 7/20; A61C 19/06; A61C 8/00; A61M 31/00
USPC ................................................ 424/53
See application file for complete search history.

(56) References Cited

U.S. PATENT DOCUMENTS

| | | | |
|---|---|---|---|
| 6,884,426 B2 | 4/2005 | Sagel et al. | |
| 7,335,025 B2 | 2/2008 | Levine | |
| 10,603,252 B2 | 3/2020 | Kim et al. | |
| 2002/0006387 A1* | 1/2002 | Sagel | A61K 8/22 424/53 |
| 2003/0003421 A1 | 1/2003 | Bestenheider et al. | |
| 2016/0287501 A1 | 10/2016 | Kim et al. | |

FOREIGN PATENT DOCUMENTS

| | | |
|---|---|---|
| CN | 105764473 A | 7/2016 |
| CN | 107949373 A | 4/2018 |
| KR | 20030000299 A | 1/2003 |
| KR | 20050119914 A | 12/2005 |
| KR | 100550066 B1 | 2/2006 |
| KR | 20170058089 A | 5/2017 |
| KR | 20170139979 A | 12/2017 |

\* cited by examiner

*Primary Examiner* — Walter E Webb
(74) *Attorney, Agent, or Firm* — Lerner David LLP

(57) ABSTRACT

A dental wrap is provided. The dental wrap includes an adhesive layer and a backing layer, which is characterized in that it does not contain an active ingredient. The present invention can improve the user's feeling of use by applying various flavors that were difficult to use in the tooth whitening agent.

14 Claims, 2 Drawing Sheets

<Wrap 1>  <Wrap 4>

DENTAL WRAP, DENTAL KIT COMPRISING THE SAME, METHOD OF USING THE SAME, AND METHOD FOR WHITENING TEETH USING THE SAME

CROSS REFERENCE TO RELATED APPLICATIONS

The present application claims priority to Korean Patent Application No. 10-2020-0004331 filed on Jan. 13, 2020 in the Republic of Korea, and Korean Patent Application No. 10-2021-0000923 filed on Jan. 5, 2021 in the Republic of Korea, the disclosures of which are incorporated in their entirety by reference.

TECHNICAL FIELD

The present invention relates to dental wrap, a dental kit comprising thereof, and a method of using thereof. More specifically, the present invention is to provide a dental wrap that can wrap the tooth surface to which a separate active ingredient for the teeth are applied, a kit for delivering the oral active ingredient to the teeth containing thereof, and a method for delivering the oral active ingredient to the teeth using thereof.

BACKGROUND ART

There are many different formulations for oral care and products with a variety of usage, but due to the nature of the oral cavity, it is affected by the moist environment, chewing and conversation. Thus, it is not easy to secure sufficient contact time to the desired area for the desired time for the active ingredient applied to the teeth or gums through various formulations and methods. It is intended to obtain the desired effect by applying drugs in various formulations such as liquid, solid, spray and the like to target areas of teeth or gums in the oral cavity. However, due to the nature of the oral cavity, it is always humid and physical movements such as talking or chewing. Thus, there was a tendency that the active ingredient did not stay in the target area for the desired contact time, and thus the desired effect was not obtained.

In general, products for attaching teeth in the form of patches are on the market for easy use, but these standardized tooth whitening patches needs a thickness of more than a certain thickness for storing drugs inevitably in order to deliver a certain amount of whitening agent effective for teeth whitening. However, due to this thickness, the flexibility of the patch was poor, so it was inconvenient for people with uneven teeth or attaching to the lower teeth. Further, in the case of tooth whitening patches, peroxide, which is most commonly used as a tooth whitening ingredient, has a problem that the compatibility of flavor and peroxide is not good, so the industry has only limited use of the type and amount of flavoring agents used in tooth whitening products. Although consumers have a great need for taste and flavor in oral products that can be directly tasted, the industry is not able to provide a suitable solution to this problem.

On the other hand, before 1990, tooth whitening technology was performed to protect the surrounding tissues such as gums by putting a rubber dam suitable for the oral cavity into the oral cavity, applying high concentration (30%) of hydrogen peroxide to the teeth, and then applying light and heat by a specialist in the dentistry (in office). Then, tooth whitening was performed by applying drugs (whitening gel, etc.) into the mouth tray that fits the teeth and then inserting the tray, or by applying the drug to the teeth and then inserting the tray in an out of office method. However, all of them had a lot of inconvenience such as time and cost. Since then, instead of using a mouth tray, a tooth whitening agent delivery system is proposed in which a tooth whitening agent is applied directly to the teeth or strip, and then a thin, transparent and flexible polyethylene strip is attached to the teeth. However, they were inconvenient to use due to the high concentration of peroxide gel being easily adhered to the hands, tongue, and gums, and due to the thick thickness of the strip, there was inconvenient to use.

DISCLOSURE

Technical Problem

The present invention is directed to providing a new dental drug delivery system, preferably a kit, which uses a composition to be applied to the oral cavity and dental wrap having excellent extensibility and a thin thickness that can cover the composition.

Further, the present invention is directed to providing a method for delivering a drug into the oral cavity, which uses dental wrap that can cover the applied composition.

Further, the present invention is directed to providing a kit including dental wrap for tooth whitening to apply various flavoring agents that have significantly decreased compatibility due to peroxide to tooth whitening products, unlike conventional tooth whitening patches.

Further, the present invention is directed to providing a dental wrap that is convenient to use and solves that problem of curling easily due to its thin thickness when peeling off the wrap from a release liner (PET layer).

Technical Solution

In one aspect of the present invention, there is provided a dental wrap, a kit for delivering an oral active ingredient to the teeth containing thereof, and a method for delivering the oral active ingredient to the teeth using thereof. The kit may be a kit for tooth whitening comprising dental wrap and a composition for tooth whitening. In another aspect of the present invention, there is provided a dental wrap, a kit for tooth whitening comprising thereof and a method for tooth whitening using thereof. The kit for tooth whitening may be a wrap-gel kit for tooth whitening comprising dental wrap and gel for tooth whitening. The kit for tooth whitening may comprise dental wrap and gel for tooth whitening, and may further comprise a manual for use of the kit. The manual may specifically guide the user how to use the dental wrap and the gel for tooth whitening.

Further another aspect of the present invention, there is provided a dental kit comprising a dental wrap and an active ingredient for the teeth that can be applied to the teeth. For example, the active ingredient for the teeth may include a tooth decay prevention ingredient, a sensitive teeth prevention ingredient and the like, and may further include other ingredients without limitation within a range that does not impair the object of the present invention.

Hereinafter, it will be described in more detail.

'About' and 'approximately' used herein may be understood as an error range of ±1 μm for thickness and an error range of ±0.1% by weight for content.

Content herein means % by weight unless otherwise specified. Further, unless otherwise specified, the total weight is based on the total weight of an adhesive layer of a dried wrap.

The present invention provides a dental wrap, a kit for delivering the oral active ingredient to the teeth containing thereof, a method for delivering the oral active ingredient to the teeth using thereof, and/or a method for tooth whitening using the kit.

The dental wrap will be described.

In one embodiment of the present invention, a dental wrap comprising an adhesive layer and a backing layer is provided, and the dental wrap does not contain an active ingredient. In one embodiment of the present invention, the dental wrap can be in the form of a thin patch, strip, film or thin membrane that is flexible enough to wrap the desired tooth area. The dental wrap of the present invention has less foreign body feeling in the oral cavity because the remaining part after covering the teeth can be folded behind the teeth.

The dental wrap has a very thin thickness, and may have a thickness of about 30 μm to 100 μm, preferably 40 μm to 70 μm, more preferably 50 μm to 60 μm. The thickness of the backing layer included in the dental wrap may be about 10 to 20 μm, or 12 to 18 μm.

The thickness can be measured with a micrometer that measures the thickness generally in the art, and for example, it can be measured using a Mitutoyo Micrometer. The dental wrap of the present invention is easy to stick to the teeth, has less foreign body feeling when attached, and can be used for a long time, so that it can be less inconvenient even when attached while sleeping. In the course of researching the present invention, the inventor of the present invention has developed a technology for separately providing a drug and making the strip thinner, focusing on the fact that the thickness of the oral patch or strip becomes thicker due to the amount of drug to be loaded for the first time.

The dental wrap may comprise an adhesive layer and a backing layer. Other layers may be further included within a range not exceeding the thickness of the dental wrap of the present invention, if necessary. The dental wrap may further comprise a release liner. The release liner is provided to protect the adhesive layer, and removed from the adhesive layer when used. The adhesive layer of the dental wrap may contain at least one polymer, more preferably a mixture of two or more of polymers selected from the group consisting of HPMC (hydroxypropyl methylcellulose), PVP (polyvinylpyrrolidone), EC (ethylcellulose) and Pullulan, but it may not contain polyquaternium, gelatin, sodium alginate, gellan gum or a mixture thereof. Preferably, the adhesive layer of the dental wrap may contain a mixture of Pullulan and PVP. When the polymers are included in the adhesive layer, it can solve the problem of curling of the wrap when peeling off the adhesive layer from the release liner and the problem that the wrap is easily broken after drying, which can occur due to the thin thickness of the dental wrap. When including a mixture of Pullulan and PVP in the adhesive layer, in order to achieve the object of the present invention, the Pullulan may be contained in an amount of 0.01 to 3% by weight, preferably 0.05 to 1% by weight based on the total weight of the dried adhesive layer, and the PVP may be contained in an amount of 30 to 60% by weight, preferably 40 to 50% by weight based on the total weight of the dried adhesive layer.

The wrap may further contain flavor. The flavor can be used without limitation in a variety of flavors generally used in oral products, and in particular, flavors such as flower, fruit, etc., which is relatively vulnerable to oxidation, that could not be used due to compatibility with peroxide, may be used. In addition to peppermint or spearmint-based flavors that are stable in hydrogen peroxide, floral flavor and fruit flavors that are easily oxidized can also be included in the kit of the present invention. The flavor included in one embodiment of the present invention can be used in a larger amount compared to the existing tooth whitening product, and may be included in an amount of 3 to 15% by weight, 4 to 10% by weight, or 5 to 8% by weight based on the total weight of the adhesive layer. Since the dental wrap of the present invention is separated from hydrogen peroxide, it may have less impact on the stability of the formulation, so that a larger amount of flavor can be used compared to general tooth whitening products.

In another embodiment, the dental wrap may comprise an adhesive layer and a backing layer, and the adhesive layer may be formed by containing only PVP, and not containing EC and HPMC.

In this embodiment, the dental wrap consists of an adhesive layer and a backing layer, and the adhesive layer contains PVP as a polymer. Loss on drying of the adhesive layer may be measured as 5 to 20%, preferably 8 to 15% based on the total weight of the adhesive layer when the wrap of 60 mm×25 mm is dried at 105° C. for 10 min. When it has the above range, it may be advantageous in achieving the object of the present invention.

In the present invention, Loss on Drying (LOD) can be obtained through the following formula.

Loss on Drying(LOD)(%)=(Weight before drying−Weight after drying)/Weight before drying×100 (%)

When PVP is used as polymer for forming an adhesive layer without EC and HPMC in the adhesive layer, in order to prevent the dental wrap from curling due to its thin thickness, the type and content of plasticizers used together can be adjusted and used. The inventors thinks that when the wrap is removed from the release liner, the adhesion between the release liner and the wrap causes the backing layer and the adhesive layer containing PVP to have different tensile levels, and thus the wrap is curled. In order to solve this problem, it was confirmed for the first time that the property of adhering well to the teeth while reducing adhesion between the release liner and the wrap is required. The plasticizer may be any one selected from polypropylene glycol, glycerin, polyethylene glycol, sorbitol, or a mixture thereof. Castor oil may not be used, and preferably glycerin may be used to solve the problem of curling of the wrap due to the nature of the thin dental wrap. Particularly, glycerin can easily control the adhesion between the wrap containing PVP and the release liner optimally, minimize curling when the wrap falls off from the release liner, and can be used as an advantageous plasticizer for laminating the adhesive layer and the backing layer.

Preferably, with respect to the weight ratio of glycerin and PVP, for PVP and glycerin, when PVP:glycerin is greater than 1:0.5, there is no problem that the adhesive layer formed by PVP and glycerin is laminated to the backing layer, and when PVP:glycerin exceeds 1:0.8, excessive stickiness may appear even after drying. Therefore, the weight ratio of glycerin and PVP may preferably be 1:0.5-0.8 (PVP:glycerin). If the content ratio of glycerin and PVP is out of the above range, the adhesion between the wrap and the release liner becomes stronger, and curling may become severe when the wrap is removed from the release liner.

In order to prevent curling due to the thin thickness of the dental wrap, in another embodiment, the dental wrap may comprise an adhesive layer and a backing layer. The adhesive layer can be formed by containing only PVP without EC and HPMC, and the adhesive layer can be maintained in a glassy state. The glassy state may mean a state in which adhesion or strength is weak in a dry state, and then gelled while being hydrated by a small amount of moisture. For example, the glassy state can be evaluated by the degree to which the adhesion in the wet state increases compared to the adhesion in the dry state by measuring the stickiness compared to the dry state with a TA/TX analyzer, and for example, it can be understood as a state in which the stickiness of 130 to 300% is increased compared to the dry state.

In addition to the polymer, plasticizer and/or flavor, the dental wrap may further contain surfactant, sweetener, pH adjusting agent and the like as necessary.

The surfactant can be used without limitation if it is a surfactant that can be used for oral products. The surfactant may be selected from HCO-40 (polyoxyethylene hydrogenated castor oil, PEG-40 Hydrogenated castor oil), SPAN 20 (sorbitan monolaurate), SPAN 40 (sorbitan monopalmitate), SPAN 60 (sorbitan monostearate), SPAN 80 (sorbitan monooleate), SPAN 85 (sorbitan trioleate), polyethylene glycol, polyethylene oxide, disodium laureth sulfosuccinate, coco-betaine, decyl glucoside, babassuamidopropyl betaine, cocamidopropyl betaine, Tween (POE sorbitan fatty acid ester)-based surfactants such as Tween 20, Tween 40, Tween 60, Tween 80, or a mixture thereof. Considering the properties of the polymer used, preferably, HCO-40 (polyoxyethylene hydrogenated castor oil, PEG-40 Hydrogenated castor oil) can be used. The surfactant can be contained in an amount of 4 to 7% by weight, 4.5 to 6.5% by weight, or 4.8 to 6% by weight based on the total weight of the dental wrap to prevent non-uniform coating due to a phenomenon in which the periphery is rolled up due to the surface tension when coating film through solvent casting.

The sweetener may include glucitol, saccharin, sucralose, stevioside, acesulfame, aspartame, xylitol, or a mixture thereof, but is not limited to these types. It can be appropriately included within the range not impairing the object of the present.

The pH adjusting agent may include at least one selected from the group consisting of sodium hydroxide, potassium hydroxide, sodium phosphate, disodium phosphate, trisodium phosphate, sodium pyrophosphate, sodium citrate, and EDTA-4Na, and preferably, it may be included in an appropriate amount so that the pH of the adhesive layer becomes 8-11. The pH of the gel applied to the tooth surface first may be acidic (about pH 3.5-4.5). At this time, when a basic wrap (approximately pH 10 to 11) is used together, the viscosity of the gel increases as the pH of the gel rises, and this makes the dental wrap well maintained on the tooth surface.

The dental wrap does not contain an active ingredient, and the active ingredient may be provided through a separate formulation or means.

In another embodiment of the present invention, when the adhesive layer contains only PVP without EC and HPMC, the adhesive layer may further include at least one polymer selected from carboxymethyl cellulose, cellulose acetate, shellac, and a mixture thereof to achieve the desired adhesion. The PVP and at least one polymer selected from carboxymethyl cellulose, cellulose acetate, shellac and a mixture thereof may be included in the adhesive layer in a weight ratio of 1:0.1 to 0.2. In the above range, it is possible to minimize the curling phenomenon occurring in the process of removing the wrap after the adhesive layer is attached to the release liner.

In order to apply the dental wrap of the present invention in a special condition of the oral cavity, the dental wrap may require a specific adhesion in consideration of all physical obstacles (for example, friction with the tip of the tongue or food), humidity and the like. Adhesion of the dental wrap of the present invention can be measured using a TA/TX analyzer.

Adhesion between the release liner and the wrap is evaluated as follows.

After attaching the release liner to the bottom of the device with double-sided tape, press it with a cylindrical tip (diameter 5 mm) with double-sided tape to attach the backing layer and the tip, and measure the force when the wrap falls from the release liner. The size of the wrap is 10 mm×25 mm. The time to press the wrap is 5 sec, the pressing force is 1000 gf, and the peeling speed is 10 mm/sec. When the wrap falls from the release liner at a room temperature of 25° C., the adhesion may be 150 to 450 gf, and preferably 180 to 400 gf.

The backing layer constituting the dental wrap is provided by being laminated on the adhesive layer, and may be a moisture impermeable film. It may comprise polypropylene, polyethylene, polyurethane or polyvinyl acetate, ethyl cellulose, polymethyl methacrylate, methacryloyl ethyl betaine/methacrylate copolymer, or a mixture thereof, and preferably, it may be polyethylene. The backing layer does not contain components used to prepare an invasive film or edible film, and for example, it does not contain starch, pectin, alginate, carrageenan, chitosan, cellulose or a derivative thereof such as hydroxypropyl methylcellulose (HPMC), Pullulan and the like. The polyethylene may preferably be LDPE (Low Density Polyethylene). The polyethylene has superior human safety to other films, is economical, has high elongation, is not easily torn (has excellent tensile strength), and, unlike other moisture-impermeable materials, it is easy to attach to the adhesive layer including a hydrophilic glassy polymer. Therefore, it can be used particularly advantageously in the wrap of the thin structure of the present invention. The backing layer can have a tensile strength of 0.5-2 kgf, and if it has a tensile strength within the above range, curling of the wrap can be reduced when it is removed from the release liner. The tensile strength can be obtained by cutting the backing layer (for example, PE film) loner than 25 mm in width and 60 mm in length, fixing it with a tensile strength measuring device (Zwick) to have a length of 60 mm, and then measuring the maximum force (kgf) until the backing layer is broken by pulling the backing layer at a speed of 30 mm per minute.

The dental wrap can be provided as one component of a patch comprising an active ingredient layer containing an active ingredient. The "active ingredient layer" may contain an active ingredient delivered to the teeth. The active ingredient layer is a dry type in which there is no adhesion or weak strength in the dry state, but when the desired area is hydrated with a small amount of water, adhesion is created or hydration begins to release the whitening agent. However, it can also be provided in a gel type that can be attached to the teeth by its own viscosity. The dental wrap may be provided by being laminated on the back side of the active ingredient layer. The dental wrap may have an embossed patter including a pocket. The presence of pockets in the embossed pattern can increase the adhesion between the active ingredient layer and the dental wrap, and the loading volume of the drug can also be increased.

The present invention provides a dental kit comprising the dental wrap.

The dental kit is provided as a kit for delivering an oral active ingredient to the teeth. The dental wrap described above may be used as a first part, and a composition including an oral active ingredient applied to the teeth may be used as a second part. In another embodiment, the dental kit may include the dental wrap described above as a first part, a composition containing an oral active ingredient applied to the teeth as a second part, and a manual for use that explain how to use the kit as a third part. The first part, the second part and the third part are not to be understood as describing an order, but to be understood as means for expressing individual separated parts.

The active ingredient is an ingredient that exerts a desired effect, for example, a tooth whitening ingredient for tooth whitening, a tooth decay prevention ingredient for tooth decay prevention, and a sensitive teeth prevention ingredient for sensitive teeth prevention. In particular, the tooth whitening ingredient is a general ingredient used in the art for a tooth whitening effect, and may include peroxide. The peroxide may not be included in the dental wrap. Since active ingredients such as peroxide are not included in the dental wrap, flavors that cannot be used due to compatibility with peroxides, and other active ingredient supplements (for example, tooth whitening aids, etc.) can be used together.

The composition containing the oral active ingredient may include a composition for tooth whitening, a composition for preventing oral diseases and the like. The composition for tooth whitening may contain a tooth whitening ingredient, and the tooth whitening ingredient may include hydrogen peroxide, carbamide peroxide, calcium peroxide, perborate, percarbonate, peroxyacids, persulfates, calcium chlorite, barium chlorite, magnesium chlorite, lithium chlorite, sodium chlorite or a mixture thereof. Any ingredient used for tooth whitening in the art may be used without limitation, and is not necessarily limited and is not interpreted to the above ingredient. The effective ingredient for preventing oral disease may be an ingredient for treating or preventing dry mouth, removal of bad breath, gingivitis, periodontal or tooth decay, or an ingredient for improving or alleviating sensitive teeth, and any ingredient used to prevent or treat oral diseases in the art can be used without limitation. For example, it may include: an antimicrobial agent including triclosan, chlorhexidine, alexidine, hexetidine, sanguinarine, benzalkonium chloride, salicylanilide, domiphen bromide, cetylpyridinium chloride (CPC), tetradecylpyridinium chloride (TPC) or a mixture thereof; an anti-inflammatory agent including aspirin, ketorolac, flurbiprofen, piroxicam, meclofenamic acid or a mixture thereof; thiamine, riboflavin, nicotinic acid, pantothenic acid, pyridoxine, biotin, folic acid, vitamin B12, lipoic acid, ascorbic acid, vitamin A, vitamin D, vitamin E, vitamin K or a mixture thereof; or a mixture thereof, but not limited thereto. Further, drugs that are effective for preventing and improving periodontal disease such as corn unsaponifiable quantitative extract, silver magnolia extract, myrrh, ratania, chamomile, polycresolene, centella quantitative extract, nutmeg extract, dexpanthenol, beta-sitosterol, acetyl salicylic acid may be included alone or in a mixture of a certain ratio. It can also include an ingredient to improve or relieve sensitive tooth symptoms containing zinc chloride, potassium phosphate, potassium diphosphate, calcium chloride, oxalic acid, potassium oxalate, ferric oxalate, vitamin E and the like alone or two or more.

The composition containing an oral active ingredient included in the dental kit may include all general formulations used when delivering drugs into the oral cavity such as gels, pastes, liquids, sprays or ointments, but a gel formulation may be desirable in consideration of ease of use, adhesion when used with a very thin dental wrap, drug loading potential, spreadability and ejectability from the container. The gel-formed dental composition may include, for example, an adhesive component such as carbomer and PVP, and carbomer is particularly preferred when considering the object of the present invention. The carbomer may be contained in an amount of 0.5 to 10% by weight, preferably 1 to 8% by weight, and 1.5 to 5% by weight based on the total weight of the composition. When the content is within the above range, adhesion with the dental wrap, spreadability and the like are excellent. When the dental composition of the present invention is applied to the tooth surface, it may have an acidic pH of about 3 to 6, preferably about pH 4 to 5, for uniform application and smooth application. In particular, when the dental wrap is attached to the tooth surface to which the composition is applied, hydrogen peroxide decomposition is accelerated and at the same time the fluidity of the gel decreases due to an increase in pH, thereby increasing adhesion. The composition may further include an adjuvant that helps increase of the effect of the medicinal ingredient. For example, ingredients such as hydrogen peroxide, glycerin, carbomer, sodium hydroxide and sodium saccharin may be mixed and included.

The container for storing the composition containing the oral active ingredient may be used quantitatively, and is not particularly limited as long as it is in a form capable of blocking contact with external oxygen. Preferably, it comprise a syringe pump with a shut-off valve.

Since the kit does not contain an oral active ingredient, especially peroxide, in the dental wrap, the flavoring agents that was not compatible with peroxide and could not be used due to deterioration during distribution in case of prolonged contact may be included in the wrap. Therefore, through the kit, since flavor and peroxide can be applied together in the oral cavity, more various flavors can be used in the kit for tooth whitening. One embodiment of the present invention includes at least one flavor selected from the group consisting of lemon, basil, *eucalyptus*, earl gray tea and the like, and can provide a kit for tooth whitening in which the flavor is present with peroxide in the oral cavity.

In one embodiment of the present invention, the kit may further contain a manual for use or guide on how to use the kit. The manual or guide may include guidelines on the proper method of discharging gel from the syringe pump, guidelines on how to use the syringe pump containing the gel, guidelines on the amount of the gel used, guidelines on how to attach and use the wrap and the like.

The guide on the amount of the gel used and how to use the gel may include the followings.

After discharging 0.2 to 0.6 g or 0.3 to 5.5 g of gel from the syringe pump, apply the gel thinly to the tooth surface so that it does not touch the gums, remove the wrap from the release liner, attach the wrap to the tooth surface, and then fold the remaining part to the back of the tooth. After applying the wrap to the teeth, breathe in to remove the saliva or moisture remaining on the tooth surface. Breathing in can be as long as a second. The wrap can be maintained for 30 to 60 minutes after application.

In addition, the kit may include a tool for applying the gel (for example, a sponge, a brush, an applicator made of rubber, etc.), and the tool may be provided in a form coupled to a container for storing the gel. In another embodiment, the kit of the present invention for delivering an oral active ingredient to the teeth may include: a) dental wrap comprising an adhesive layer, which contains at least one selected from the group consisting of HPMC (hydroxypropyl methylcellulose), PVP (polyvinylpyrrolidone), EC (ethylcellulose) and Pullulan, but dose not contain the oral active ingredient, and a backing layer laminated on the adhesive layer; and b) a container in which the composition containing the oral active ingredient is stored. The container may further include a tool for applying the composition of a) to the tooth surface.

Guide on how to use the tool for applying the gel may also be included in the kit. The kit may further include a tool for removing moisture or the saliva left on the tooth surface before applying the gel to the tooth surface. For example, after wiping the tooth surface using an applicator made of a material having good moisture absorption, the gel is applied, and the gel and wrap are well adhered to the tooth surface by the applicator.

Another embodiment of the present invention provides a method for delivering an oral active ingredient to the teeth and a method for whitening teeth using thereof.

In one embodiment, the method may comprise the following steps of:

S1) treating a composition containing an oral active ingredient to the teeth; and S2) wrapping the teeth treated with the oral active ingredient with dental wrap comprising an adhesive layer, which contains at least one selected from the group consisting of HPMC (hydroxypropyl methylcellulose), PVP (polyvinylpyrrolidone), EC (ethylcellulose) and Pullulan, but dose not contain the oral active ingredient, and a backing layer laminated on the adhesive layer.

Another embodiment provides a method for tooth whitening, which comprises the following steps of:

S1) treating a composition containing an ingredient for tooth whitening to the teeth; and S2) wrapping the teeth treated with the composition with dental wrap comprising an adhesive layer, which contains at least one selected from the group consisting of HPMC (hydroxypropyl methylcellulose), PVP (polyvinylpyrrolidone), EC (ethylcellulose) and Pullulan, but dose not contain the oral active ingredient, and a backing layer laminated on the adhesive layer.

Another embodiment may further include a step of removing moisture and/or the saliva form the tooth surface before the S1) step, but the removal step may not be essential. In the case of wrapping the teeth, depending on the purpose, one, two, three, four, five, six, seven, eight or more teeth may be wrapped. The wrapping means a shape that covers the tooth surface, and the portion remaining after covering the tooth surface may be folded to the back of the tooth.

Advantageous Effects

The present invention can improve the user's feeling of use by applying various flavors that were difficult to use in the tooth whitening agent. In the present invention, when peeling off the wrap from the release liner (PET layer), it is not easily curled up and can be easily separated from the release liner despite the thin thickness.

The kit for tooth whitening of the present invention has little foreign body feeling even if the wrap is attached to the tooth surface overnight, and it is easy to keep it attached to the tooth surface.

Since the dental wrap does not contain peroxide, flavor compositions that are not compatible with peroxides and have been deteriorated in the distribution process during long-term contact can be included in the wrap. Therefore, it is possible to apply flavor and peroxide in the oral cavity through the kit, so that more various flavors can be used for the kit for tooth whitening.

DESCRIPTION OF DRAWINGS

The accompanying drawings illustrate a preferred embodiment of the present invention and together with the foregoing invention, serve to provide further understanding of the technical features of the present invention, and thus, the present invention is not construed as being limited to the drawing.

MODE FOR DISCLOSURE

Hereinafter, in order to describe the present invention in more detail, it will be described with reference to the following embodiments. However, the embodiments according to the present invention may be modified in various forms, and the scope of the present invention should not be construed as being limited to the embodiments described below. The embodiments of the present invention are provided by way of example to aid in a specific understanding of the present invention. Unless otherwise specified, % described herein can be understood to mean % by weight.

[Dental Gel-Wrap Drug Delivery System]

Figure 1:
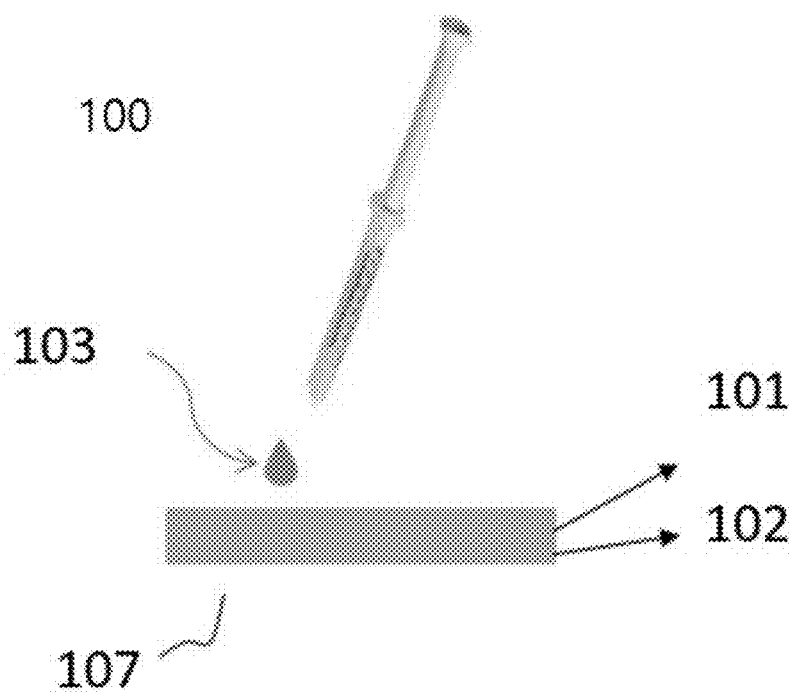
FIG. 1 is a diagram schematically illustrating a kit including gel for whitening the teeth and wrap for attaching the teeth according to an embodiment of the present invention.

As follows, a kit including gel and wrap was prepared. In FIG. 1, the kit 100 includes wrap 107 and gel 103. The wrap 107 includes an adhesive layer 101 and backing layer 102. This kit includes an active ingredient for whitening teeth in the gel, and the wrap includes flavor, but does not include an active ingredient for whitening teeth. Table 1 below shows the composition of the gel, and Table 2 below shows the composition of the adhesive layer of the wrap.

TABLE 1

| Ingredient | Gel |
| --- | --- |
| Hydrogen peroxide | 6.0 |
| Glycerin | 20.0 |
| Carbomer | 1.8 |
| Sodium hydroxide | 0.08 |
| Sodium saccharin | 0.1 |
| Purified water | To 100 |

TABLE 2

| Ingredient | Wrap1 | Wrap2 | Wrap3 | Wrap4 |
| --- | --- | --- | --- | --- |
| Glycerin | 26.6 | 34.0 | 30.2 | 33.1 |
| HCO-40 | | | 5.0 | 4.4 |
| SPAN80 | 3.3 | | | |
| PVP | 59.2 | 42.5 | 47.7 | 44.2 |
| Pullulan | | | | 0.05 |
| HPMC | | | 5.0 | |
| EC | | 8.5 | | |
| Sodium phosphate tribasic | 1.5 | | 1.5 | 1.5 |
| Sodium hydroxide | | 0.3 | | |
| Saccharin | 0.6 | 0.6 | 0.5 | 0.5 |
| Flavor | 5.6 | 5.7 | 5.0 | 5 |
| Ethanol | | 2.8 | | |
| Purified water | To 100 | To 100 | To 100 | To 100 |

The manufacturing method is as follows.

Gel—Raw materials excluding a neutralizing agent are added to a mixing tank, stirred homogeneously, and after confirming that there is no dissolution or lumped mass, carbomer is neutralized to increase the viscosity. The viscosity is adjusted in the range of 20,000 to 480,000 after rotation using Brookfield Viscometer (RV) Spindle No. 7 at 20 rpm for 15 seconds.

Wrap—After putting raw materials into a mixing tank and stirring it homogeneously, the mixture was applied to a certain thickness using a comma coater, dried by blowing dry hot air (40-60° C.), and then the backing layer (Low density polyethylene (LDPE)) was laminated thereto. (Solvent casting)

[Method of use]

Gels and wraps having the compositions of Table 1 and Table 2 above were prepared, respectively, and used for tooth whitening. The gel was used in a fixed amount, and stored in a syringe pump with a shut-off valve to prevent leakage. A fixed amount of gel discharged from the syringe pump was applied to the tooth surface. When used about 0.2-0.6 g per use, the gel flows into the teeth as well as the tooth surface, so it was effective for whitening between teeth.

The wrap was detached from the release liner and then attached to the tooth surface.

[Tackiness Measurement]

Figure 2:
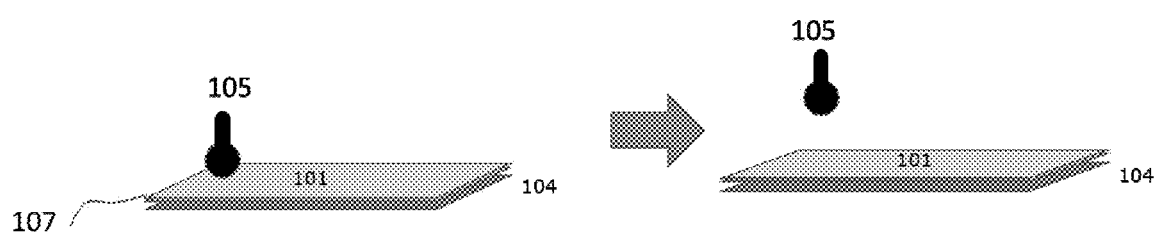
FIG. 2 is a diagram schematically illustrating a method for measuring Ball tackiness.

It was measured using a TA/TX analyzer. After attaching the backing layer of the wrap product to the bottom of the device using double-sided tape, the release liner was remove from the adhesive layer and the Ball tackiness was measured. (Dry/Wet) The experimental method is schematically shown in FIG. 2. In FIG. 2, the wrap 107 was attached to double-sided tape 104. Once the wrap was attached, a ball 105 was placed on the adhesive layer of the wrap 101. After a specific amount of time, the ball 105 was removed from the adhesive layer 101.

Wetting method: Purified water is sprayed once using a spray.

Pressing time (5 sec), Pressing force (5 gf), Peeling speed (10 mm/sec) Adhesion according to the prescription is shown in Table 3.

TABLE 3

|  | F Max(gf) | F Min(gf) | F average(gf) (S.D.) |
|---|---|---|---|
| Wrap 1 | 150.1 | 66.7 | 110.7 (35.039) |
| Wrap 2 | 143.9 | 80.0 | 115.1 (26.914) |
| Wrap 3 | 43.1 | 21.7 | 29.5 (10.041) |
| Wrap 4 | 99.3 | 78.5 | 91.6 (11.378) |

*F Max(gf): Maximum force until falling,
F Min(gf): Minimum force until falling

Adhesion according to wetting is shown in Table 4.

TABLE 4

| Number | Wetting | F Max(gf) | F Min(gf) | F average(gf) (S.D.) |
|---|---|---|---|---|
| Wrap 4 | Dry | 99.3 | 78.5 | 91.6 (11.378) |
|  | Wet | 178.3 | 143.1 | 161.0 (17.638) |

Figure 3:
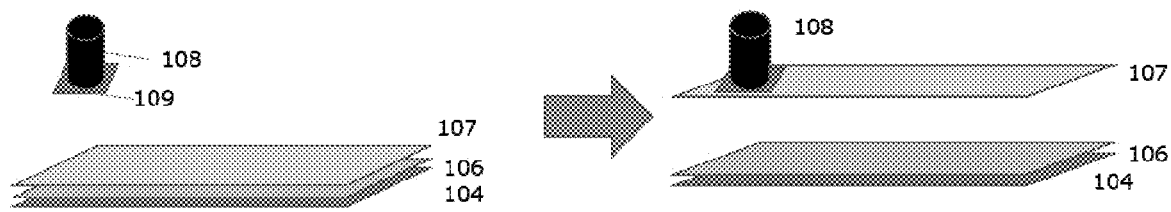
FIG. 3 is a diagram illustrating a process of measuring the force when peeling off wrap from PET.

The force when peeling off the Wrap from PET was measured, and the experimental method is shown in FIG. 3. The TA/TX analyzer was used.

As illustrated in FIG. 3, after attaching the release liner of the Wrap product 106 to the bottom of the device using double-sided tape 104, the backing layer and a cylindrical tip (diameter 5 mm) 108 were attached by pressing the backing layer with the tip with double-sided tape 109 attached. Then, the force when the Wrap fell from the release liner was measured, and the tip was attached to one end of the Wrap size (10 mm×25 mm).

Pressing time (5 sec), Pressing force (1000 gf), Peeling speed (10 mm/sec)

TABLE 5

| Number | F Max(gf) | F Min(gf) | F average(gf) (S.D.) |
|---|---|---|---|
| Wrap 1 | 733.8 | 665.3 | 710.7 (39.338) |
| Wrap 2 | 351.0 | 245.9 | 308.0 (55.055) |
| Wrap 3 | 325.2 | 225.4 | 274.6 (53.096) |
| Wrap 4 | 362.5 | 200.8 | 306.7 (91.744) |

[Comparison of Wrap Curling Degree]

Figure 4:
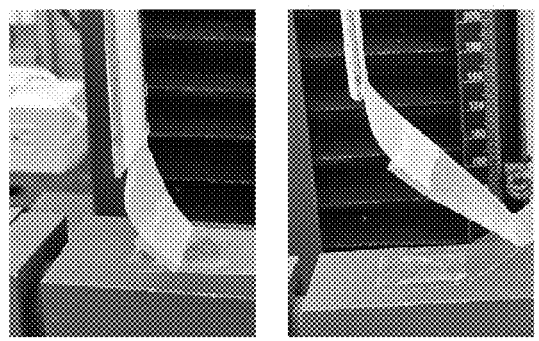
FIG. 4 illustrates a process of measuring the curling degree of wrap.

The experimental method is as follows, and is illustrated in FIG. 4.

1. After uniformly cutting the Wrap into 70 mm in length and 20 mm in width, the release liner is attached and fixed to the bottom of the device using double-sided tape.

2. Using tape, Zwick universal tester and the backing layer of the Wrap are attached.

3. The Wrap was peeled off from the release liner by pulling at a certain speed. (13 mm/sec)

4. The length of the Wrap was measured without unfolding the Wrap again.

The curling results using the wrap of Table 2 are shown in Table 6 below.

TABLE 6

| Number | Length after peeling (mm) |
|---|---|
| Wrap 1 | 44 |
| Wrap 2 | 63 |
| Wrap 3 | 62 |
| Wrap 4 | 68 |

Figure 5:
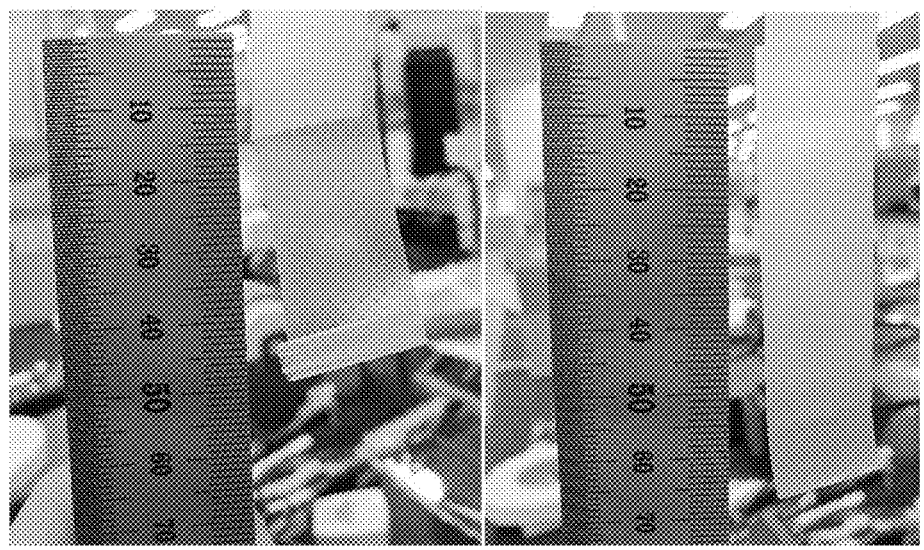
FIG. 5 illustrates the results of measuring the length after peeling of Wrap 1 and Wrap 4.

Wrap 1 was easily curled up when peeling, so that length was shortened. A photograph of the experimental results of Wrap 1 and Wrap 4 is shown in FIG. 5.

What is claimed is:

1. A dental wrap comprising an adhesive layer and a backing layer, wherein the dental wrap does not contain an active ingredient, wherein the adhesive layer includes PVP and Pullulan, wherein the Pullulan is included in an amount of 0.01 to 3% by weight based on a total weight of dried adhesive layer, and the PVP is included in an amount of 40 to 60% by weight based on the total weight of the dried adhesive layer.

2. The dental wrap of claim 1, further including a flavor in an amount of 3 to 15% by weight based on a total weight of the adhesive layer.

3. The dental wrap of claim 1, wherein the adhesive layer does not contain EC and HPMC, but contains PVP.

4. The dental wrap of claim 3, wherein the adhesive layer further includes glycerin as a plasticizer.

5. The dental wrap of claim 4, wherein the PVP and the glycerin are included in the adhesive layer in a weight ratio of 1:0.5-0.8 (PVP:glycerin).

6. The dental wrap of claim 3, wherein the adhesive layer includes a surfactant in an amount of 4 to 7% by weight based on a total weight of the adhesive layer.

7. The dental wrap of claim 3, wherein the adhesive layer further includes an additional polymer, wherein the additional polymer is selected from the group consisting of carboxymethyl cellulose, cellulose acetate, shellac and a mixture thereof.

8. The dental wrap of claim 7, wherein the PVP and the additional polymer are included in the adhesive layer in a weight ratio of 1:0.1 to 0.2.

9. The dental wrap of claim 1, having an embossed pattern including a pocket.

10. The dental wrap of claim 1, having a thickness of 30 μm to 100 μm.

11. A kit for delivering an oral active ingredient to the teeth, comprising:
   a) a dental wrap including:
   an adhesive layer, wherein the adhesive layer includes PVP and Pullulan,
   wherein the Pullulan is included in an amount of 0.01 to 3% by weight based on a total weight of dried adhesive layer, and the PVP is included in an amount of 40 to 60% by weight based on the total weight of the dried adhesive layer, and does not contain the oral active ingredient, and
   a backing layer laminated on the adhesive layer; and
   b) a composition containing the oral active ingredient.

12. The kit of claim 11, further comprising c) a manual for use.

13. The kit of claim 11, wherein b) the composition containing the oral active ingredient contains carbomer in an amount of 0.5 to 10% by weight based on a total weight of the composition.

14. A method for tooth whitening, comprising:
   S1) treating a composition containing an ingredient for tooth whitening to the teeth; and
   S2) wrapping the teeth treated with the composition with a dental wrap comprising an adhesive layer, and a backing layer laminated on the adhesive layer,
   wherein the adhesive layer contains PVP and Pullulan, wherein the Pullulan is included in an amount of 0.01 to 3% by weight based on a total weight of dried adhesive layer, and the PVP is included in an amount of 40 to 60% by weight based on the total weight of the dried adhesive layer, and does not contain the oral active ingredient.

* * * * *